United States Patent [19]
Yoshida et al.

[11] Patent Number: 5,446,537
[45] Date of Patent: Aug. 29, 1995

[54] METHOD OF SORTING SEMICONDUCTOR LASERS

[75] Inventors: Ichiro Yoshida; Tsukuru Katsuyama; Jun-ichi Hashimoto, all of Yokohama, Japan

[73] Assignee: Sumitomo Electric Industries, Ltd., Osaka, Japan

[21] Appl. No.: 268,534

[22] Filed: Jul. 6, 1994

[30] Foreign Application Priority Data

Jul. 13, 1993 [JP] Japan .................................. 5-173249
Jul. 1, 1994 [JP] Japan .................................. 6-151062

[51] Int. Cl.⁶ ............................................ G01N 21/88
[52] U.S. Cl. ............................................ 356/256
[58] Field of Search ........................... 356/237, 256

[56] References Cited

U.S. PATENT DOCUMENTS 5,116,767 5/1992 De Chiaro et al. ................... 437/7

FOREIGN PATENT DOCUMENTS 60-198793 10/1985 Japan.
1-529912 11/1989 Japan.

OTHER PUBLICATIONS

Patent Abstracts of Japan, Abstract of 60-198793, Oct. 8, 1985, ABS GRP No: E382, No. 42, vol. 10.

*Primary Examiner*—F. L. Evans
*Attorney, Agent, or Firm*—Beveridge, DeGrandi, Weilacher & Young

[57] ABSTRACT

It is an object to provide a method of sorting semiconductor lasers, capable of appropriately removing semiconductor lasers which can cause a so-called sudden death in use. After a first current within a range of 50 to 150% the maximum rated current is supplied to the semiconductor lasers for a predetermined period of time, a second current is supplied within a range of 120 to 250% the maximum rated current for a short period of time. Semiconductor lasers which are destroyed or degraded in output characteristics are removed as defective devices.

10 Claims, 3 Drawing Sheets

METHOD OF SORTING SEMICONDUCTOR LASERS

BACKGROUND OF THE INVENTION

1. Field of the Invention

The present invention relates to a method of sorting non-defective/defective semiconductor lasers and, more particularly, to a sorting method appropriately used for semiconductor lasers having a GaInAs active layer and emitting a light with a oscillating wavelength of about 0.98 μm.

2. Related Background Art

A semiconductor laser having a GaInAs active layer and emitting a light with a oscillating wavelength of about 0.98 μm is desired to be put to practical use as an exciting light source of an Er-doped optical fiber amplifier. For this purpose, defective devices must be appropriately removed. As a sorting method of removing defective semiconductor lasers, a so-called accelerated test is generally used. In this method, a current larger than that in actual use is supplied for a predetermined period of time to remove initial detects. To acknowledge the initial defects, for example, a method on the basis of a change in threshold current before and after the accelerated test is used (Japanese Patent Publication No. 1-52912).

In the semiconductor lasers having a GaInAs active layer, however, rapid degradation occurs from one point during energization so that the semiconductor lasers reach a destruction state, i.e., a so-called sudden death is observed even in devices determined to be non-defective by the conventional accelerated test. That is, although the devices seem to have the same characteristics as those of a normal sample without exhibiting an increase in driving current to that point, they are suddenly degraded. Because of the high probability of such a sudden death in use, the GaInAs semiconductor lasers have not been widely used yet.

SUMMARY OF THE INVENTION

It is an object of the present invention to provide a sorting method capable of appropriately removing defective semiconductor lasers which come to a sudden death in use.

In order to achieve the above object, according to the present invention, there is provided a method of sorting semiconductor lasers, comprising
the first step of supplying a first current within a range of 50 to 150% a maximum rated current to the semiconductor lasers for at least 50 hours,
the second step of supplying a second current larger than the first current within a range of 120 to 250% the maximum rated current for at least 1 microsecond after the first step, and
the third step of measuring light output characteristics after the second step and removing defective devices in accordance with a measurement result.

According to the present invention, there is also provided a method of sorting semiconductor lasers, comprising
the first step of causing the semiconductor lasers to output a first light output within a range of 50 to 150% a maximum rated light output for at least 50 hours,
the second step of causing the semiconductor lasers to output a second light output larger than the first light output within a range of 120 to 250% the maximum rated light output for at least 1 microsecond after the first step, and
the third step of measuring light output characteristics after the second step and removing defective devices in accordance with a measurement result.

In both the sorting methods, the ambient temperature during supplying the first current or outputting the first light output is preferably higher than room temperature (25° C.).

According to the studies of the present inventors, the sudden death of a GaInAs semiconductor laser is caused due to melting of an end face. This is called so-called catastrophic optical damage (COD) and assumed to be caused by the interaction of the light and the current at the end face. Although the semiconductor laser is operated at a predetermined density of light, the COD occurs at one point during energization because the COD level (light output value at which the COD occurs) is decreased during energization. When the COD level is decreased to the light output value in the energization conditions in use, a sudden death occurs.

According to the present invention, the first current within a range of 50 to 150% the maximum rated current is supplied for a predetermined period of time to forcibly decrease the COD level. With this operation, the difference in the COD level between a non-defective device and a defective device is increased. In the non-defective device, the COD level is only slightly decreased, and the COD level is kept relatively high even after the first current is supplied. However, in the defective device, the COD level is low from the beginning, or although the COD level is originally high, it is largely decreased. The COD level of the defective device after the first current is supplied is thus much lower than that of the non-defective device. In this state, when the second current is instantaneously supplied, almost all of the defective devices are destroyed. Since the second current is supplied for a very short period of time, the COD level of the non-defective devices is hardly decreased.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

Figure 1:
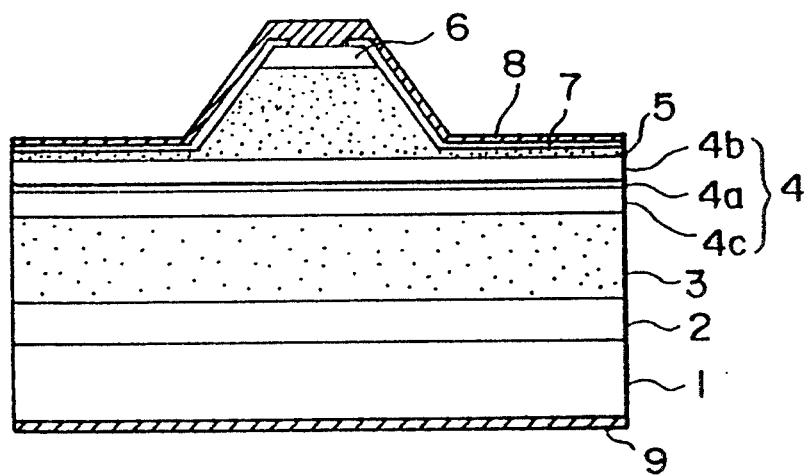
FIG. 1 is a sectional view showing a semiconductor laser to which a sorting method of the present invention is applied.

FIG. 1 is a sectional view showing the structure of a semiconductor laser subjected to a sorting method of the present invention. This structure will be briefly described. An Si-doped n-type GaAs buffer layer 2, an Si-doped n-type GaInP cladding layer 3, a GaInAs active layer 4, a Zn-doped p-type GaInP cladding layer 5, and a Zn-doped p-type GaAs contact layer 6 are epitaxially grown on an Si-doped n-type GaAs substrate 1. The GaInAs active layer 4 is constituted such that a GaInAs quantum well layer 4a is sandwiched between light confinement layers 4b and 4c. The p-type GaAs contact layer 6 and the p-type GaInP cladding layer 5 are mesa-etched as shown in FIG. 1. An SiN film 7 is formed on the surface of the resultant structure except for the top portion of the mesa. A p-side electrode 8 is formed on the resultant structure, and an n-side electrode 9 is formed on the lower surface of the GaAs substrate 1. The width of a stripe is 5 μm at the bottom portion of the mesa, and the length of a resonator is 1 mm. The p-side electrode 8 and the contact layer 6 are removed by a length of about 20 μm from a portion near the end face, thereby preventing easy flow of a current. This structure allows a slow decrease in the COD level. A light-reflecting film having a low reflectance of 5% is formed on the front surface of this chip, and a light-reflecting film having a reflectance of 90% is formed on the rear surface.

A sorting method according to an embodiment of the present invention applied to this semiconductor laser will be described below. Assume that the maximum rated current of the semiconductor lasers subjected to sorting is, e.g., 300 mA. The maximum rated current means the maximum value of a driving current for guaranteeing the use of the semiconductor laser. The maximum rated current is one of design specifications.

First of all, a first current of 275 mA, which corresponds to 91.7% the maximum rated current, is supplied at 50° C. for 100 hours. Thereafter, a second current of 485 mA, which corresponds to 161.7% the maximum rated current, is supplied at room temperature for several seconds. Semiconductor lasers destroyed in this process are removed, and the remaining lasers are acknowledged as non-defective devices.

Figure 2:
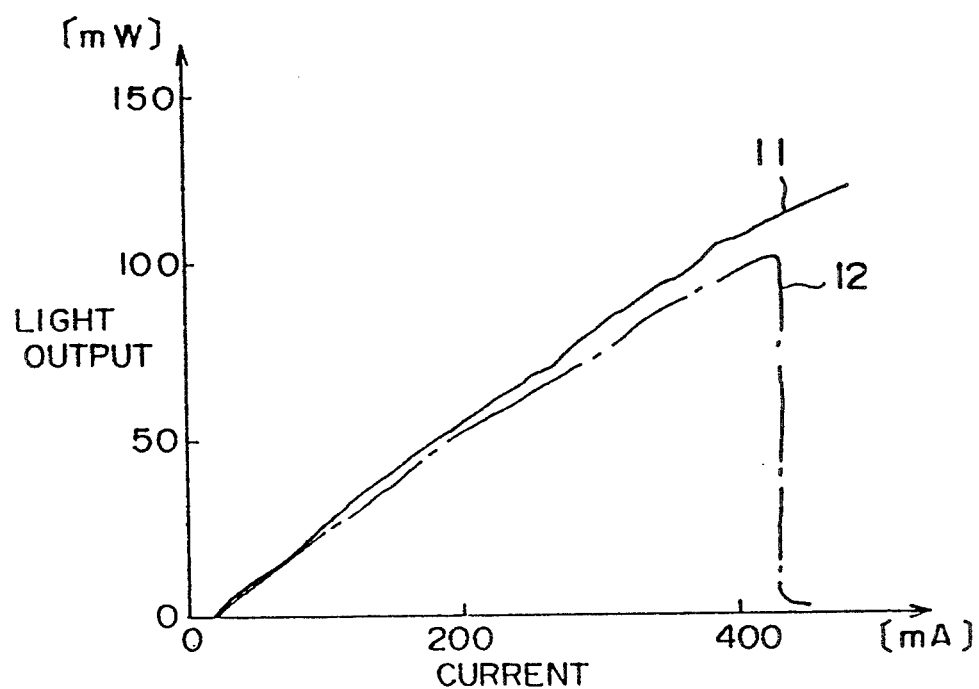
FIG. 2 is a chart showing light output characteristics of a semiconductor laser determined to be defective by the sorting method according to an embodiment of the present invention.
Figure 3:
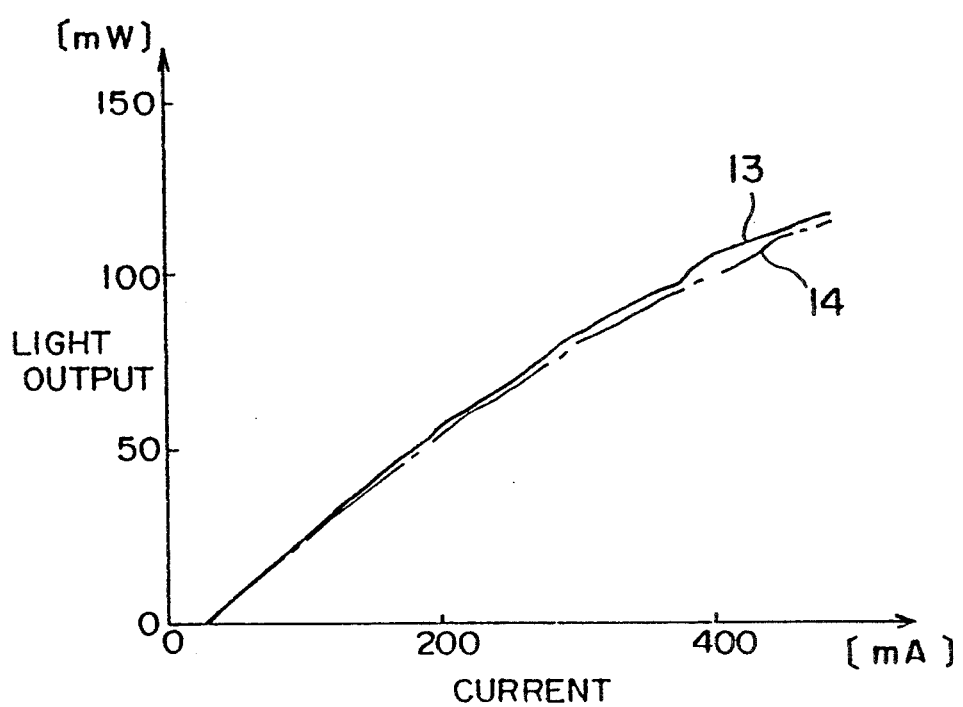
FIG. 3 is a chart showing light output characteristics of a semiconductor laser determined to be non-defective by the sorting method according to the embodiment of the present invention.

FIGS. 2 and 3 are charts showing the light output characteristics of a defective sample and a non-defective sample, respectively. Referring to FIGS. 2 and 3, solid lines 11 and 13 represent measurement results before the first current is supplied, and chain lines 12 and 14 represent measurement results after the first current is supplied. In both the measurements, the driving current was continuously changed within a range of 0 to 485 mA. Therefore, the measurement represented by the chain line is one process of this embodiment for removing defective semiconductor lasers destroyed upon supplying the second current.

In the non-defective devices, as is apparent from FIG. 3, the characteristics are not so changed even after the first energization. Also in the defective devices, the characteristics are not so changed after the first energization as far as the supplied current is as large as two or three times the current in actual use, i.e., when the supplied current is as large as the maximum rated current by a few times. However, as the current is increased, a slight decrease in light output after the first energization is observed. When a current of about 420 mA was supplied, the COD occurred to stop the laser oscillation. The semiconductor lasers destroyed upon supplying the second current are assumed to have been largely decreased in COD level upon the first energization, or originally low in COD level. Therefore, if these semiconductor lasers are determined to be non-defective and put to use because they are hardly degraded upon the first energization, the semiconductor lasers are anticipated to be destroyed due to a sudden death in use. To the contrary, for the semiconductor lasers not destroyed by applying the sorting method of this embodiment, the probability of sudden death is very low even if they are used for a long period of time. Note that the semiconductor lasers which exhibit difference of 10% or more in light output between the start and the end of the first energization can be acknowledged as defective at that point. The semiconductor lasers which exhibit great degradation in characteristics although not completely destroyed upon the second energization are also preferably acknowledged as defective. The energization time of the second current must be a enough time for semiconductor lasers having low COD level to be destroyed due to COD. According to experimental results, it's necessary that the second current is supplied for at least 1 micro-second.

In some samples, the optical outputs satulate due to heat generation at the active layers. In such case, pulse current whose width is longer than 1 micro-second is useful as a driving source. A pulse current source which can supply shorter than 1 micro-second width pulse current is very expensive. And when the pulse width is shorter than 1 micro-second, the samples may not destroy due to COD.

In this embodiment, the second current is set to 485 mA. However, when this current is increased, the average service life of the semiconductor lasers determined to be non-defective can be prolonged although the yield is decreased. The second current value should be determined in accordance with the service life to be guaranteed and the fraction defective, as in the first current value. Actually, however, this must be led out from the empirical rule. If data cannot be sufficiently obtained, the following method can be effectively used. First of all, the current value which causes the COD is measured using some samples obtained by the same processes as those used for the target semiconductor lasers. The second current value is set to 70% the average value. If the semiconductor laser samples are not destroyed due to the COD and their outputs are limited by thermal saturation, the second current is set to 80% the average value of the current for allowing the maximum output. The first current is set to 50% the second current. The temperature and the time of supplying the first current are set to 50° C. and 100 hours, respectively.

As described above, according to this embodiment, detective devices which are not easily detected even by the accelerated degradation process by the first energization can be appropriately removed.

In the above embodiment, the second current is supplied at room temperature. However, when energization is performed at a lower temperature, the light output is increased, so the second current value can be set to a lower value without changing the light output. In this case, an inexpensive current supplying apparatus can be expected to be used. In addition, in the above embodiment, one second current value is set for a plurality of samples to which the sorting method is applied, and this second current value is applied to all the target samples. The second current value can be appropriately selected in accordance with the to-be-sorted semiconductor lasers. Furthermore, in place of the fixed second current value, the second current may be supplied such that the light output is fixed. More specifically, the second current may be supplied such that a light output within a range of 120 to 250% the maximum rated light output (e.g., a light output of 130 mW) is obtained. Similarly, the first current may also be defined not by the current but by the light output.

According to experiments by the present inventors, when the first current was supplied within a range of 50 to 150% the maximum rated current for at least 50 hours, and the second current larger than the first current was supplied within a range of 120 to 250% the maximum rated current, a sufficient effect for removal of defective devices was obtained.

The first current value and the energization time of the first current will be considered together with the experimental results. An uncoated semiconductor laser (its maximum rated current is 300 mA) having the structure shown in FIG. 1 was mounted on a copper heat sink using gold tin with the substrate 1 side facing downward. In a coated device, the degradation rate of the COD level is decreased. Therefore, when an uncoated device is used as in this experiment, the test is performed in severer conditions. A current was supplied up to 500 mA at 25° C. or 50° C. to measure the characteristics, and initial defective devices (e.g., devices having a very high threshold value) were removed. These remaining samples were divided into nine groups each including 7 to 8 samples, and the energization test was performed using the first current at 50° C. After a predetermined period of time, energization of the samples was stopped. A current (second current) was supplied up to 500 mA at 50° C. for a short period of time to measure the current vs. light output characteristics. The first current and the energization time of the first current were as follows.

| Current (mA) | Energization time (hours) |
| --- | --- |
| 275 | 100 |
| 275 | 400 |
| 275 | 1033 |
| 350 | 50 |
| 350 | 300 |

The COD level is decreased by this energization. Therefore, the devices which were normally operated before energization even when a current of 500 mA was supplied are destroyed due to COD. The Weibull distribution of the COD level was made to obtain the characteristic COD level. The characteristic COD level means that the 1/e (e is the base of natural logarithm) devices of all the samples have a value equal to or larger than the level. In other words, when an operating current is supplied to all the samples such that an output at the characteristic COD level can be obtained, (1-1/e) devices of the all samples are COD-destroyed. Note that an m value of the Weibull distribution was about 13.

Figure 4:
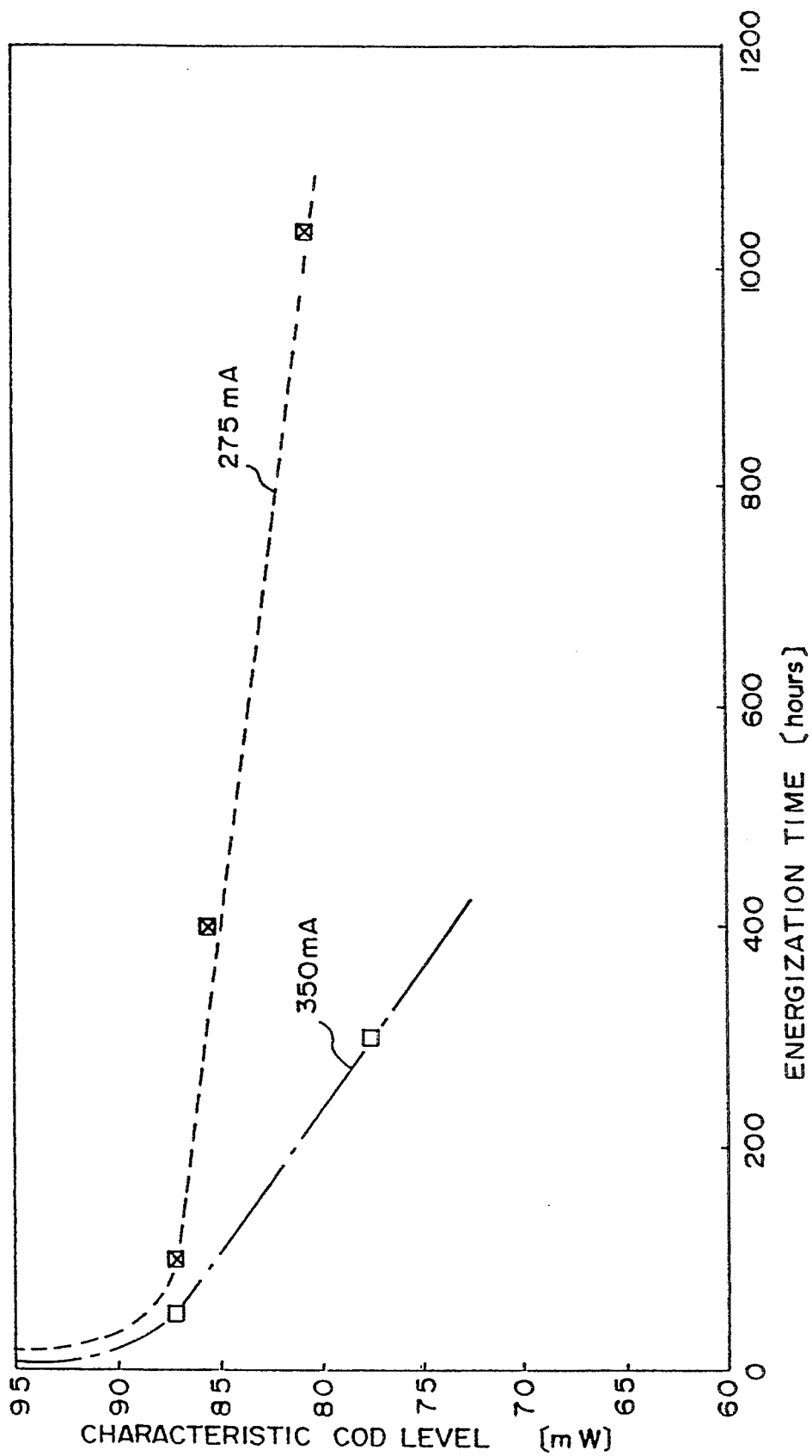
FIG. 4 is a graph showing the relationship between the energization time of a first current and a characteristic COD level.

The result is shown in FIG. 4. Referring to FIG. 4, the energization time of the current is plotted along the abscissa, and the characteristic COD level is plotted along the ordinate. The characteristic COD level before this energization is found to be 104 mW or more. This is because, before energization, few devices were degraded at a current of 500 mA or less, and the average output at a current of 500 mA was 104 mW. If the first current is supplied to these samples, the COD level is largely decreased within the first 50 hours of energization not only when the current value is 275 mA but also it is 350 mA. The characteristic COD level was 88 mW at both the supplied current values. The characteristic COD level after 50 hours is gradually decreased at almost a predetermined rate in accordance with the current value.

The dependency of the degradation rate of the characteristic COD level on the current can be obtained from this data. When the degradation rate was assumed to be proportional to a current value to the $\alpha$th power, $\alpha$ was about 10. That is $$\log (dp_{cod}/dt) = \alpha \log (I) - 24.8$$

where $P_{cod}$ represents a characteristic COD (mW), t represents a time (hours), I represents a current (mA), and log represents the natural logarithm.

The second current will be considered below.

In the sample devices used in this experiment, the current for obtaining a light output of 50 mW at 50° C. was 200 mA. The degradation rate of the characteristic COD level at this time was assumed to be $2.0 \times 10^{-4}$ mW/h. From these data, for example, if this laser is used at 50° C. and a light output of 50 mA, it can be estimated that the COD destruction will occur within 100,000 hours (about ten years). In this experiment, a value of 1.71% was obtained. If this laser is used at room temperature, the degradation rate of the COD level is assumed to be lower than that at 50° C., and the value of 1.71% is considered to be almost the worst value.

Therefore, when the second value is selected such that 1.71% or more, e.g., 5% of all the samples cause the COD destruction when they are used in conditions corresponding to the output of 50 mW of an uncoated device (or milder conditions), the reliability of the remaining devices can be guaranteed.

As has been described above, by using the method of sorting the semiconductor lasers of the present invention, semiconductor lasers which reach the so-called sudden death in use can be appropriately removed in advance. In other words, semiconductor lasers left after the sorting method of the present invention was used are stably operated for a long period of time at very high probability.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 173249/1993 filed on Jul. 13, 1993 and No. 151062/1994 filed on Jul. 1, 1994 are hereby incorporated by reference.

What is claimed is:

1. A method of sorting semiconductor lasers, comprising:
   the first step of supplying a first current within a range of 50 to 150% a maximum rated current to said semiconductor lasers for at least 50 hours;
   the second step of supplying a second current larger than the first current within a range of 120 to 250% the maximum rated current for at least 1 microsecond after the first step; and the third step of measuring light output characteristics after the second step and removing defective devices in accordance with a measurement result.

2. A method according to claim 1, wherein the second step includes the steps of measuring a relationship between the supplied current and a light output and using a measurement result as the light output characteristics to be measured in the third step.

3. A method according to claim 1, wherein the third step includes the steps of supplying a predetermined current to said semiconductor lasers and determining and removing said semiconductor lasers to be defective when a light output value at that time is smaller than a predetermined value.

4. A method according to claim 1, wherein an ambient temperature in the first step is higher than room temperature (25° C.).

5. A method according to claim 1, wherein an ambient temperature in the second step is lower than an ambient temperature in the first step.

6. A method of sorting semiconductor lasers, comprising:

the first step of causing said semiconductor lasers to output a first light output within a range of 50 to 150% a maximum rated light output for at least 50 hours;

the second step of causing said semiconductor lasers to output a second light output larger than the first light output within a range of 120 to 250% the maximum rated light output for at least 1 microsecond after the first step; and the third step of measuring light output characteristics after the second step and removing defective devices in accordance with a measurement result.

7. A method according to claim 6, wherein the second step includes the steps of, when the second light output is output, measuring a relationship between a supplied current and the light output and using a measurement result as the light output characteristics to be measured in the third step.

8. A method according to claim 6, wherein the third step includes the steps of supplying a predetermined current to said semiconductor lasers and determining and removing said semiconductor lasers to be defective when a light output value at that time is smaller than a predetermined value.

9. A method according to claim 6, wherein an ambient temperature in the first step is higher than room temperature (25 ° C.).

10. A method according to claim 6, wherein an ambient temperature in the second step is lower than an ambient temperature in the first step.

* * * * *